United States Patent [19]

Daunora

[11] 4,347,235

[45] Aug. 31, 1982

[54] WATER-SOLUBLE TABLET

[75] Inventor: Louis G. Daunora, Lakewood, Colo.

[73] Assignee: Miles Laboratories, Inc., Elkhart, Ind.

[21] Appl. No.: 299,122

[22] Filed: Sep. 3, 1981

[51] Int. Cl.$^3$ .......................... A61K 2/46; A61K 9/20; A61K 31/765
[52] U.S. Cl. .......................................... 424/44; 424/78
[58] Field of Search ..................................... 424/44, 78

[56] References Cited

U.S. PATENT DOCUMENTS 2,540,253  2/1951  Gakonheimer ........................ 424/44
3,926,817  12/1975  Nakajima et al. ..................... 424/44
3,976,601  8/1976  Levin .................................... 424/44

FOREIGN PATENT DOCUMENTS 54-86622  7/1979  Japan .

OTHER PUBLICATIONS

Spitael et al., Pharm. Ind. 39(5):502–505 (1977).
Saeki S. et al., Polymer 1977 18(10):1027–1031.
Hoerland H., J. Chem. Soc. Faraday Trans. 1 (1976) 72(6):1441–1447.
Kaulgud et al., Indian J. Chem. 13(6):616–617 (1975).

*Primary Examiner*—Shep K. Rose
*Attorney, Agent, or Firm*—J. D. McNeil

[57] ABSTRACT

An improved water-soluble tablet is disclosed. The tablet includes sodium propionate or a combination of sodium propionate and polyethylene glycol.

8 Claims, No Drawings

WATER-SOLUBLE TABLET

BACKGROUND OF THE INVENTION

1. Field of the Invention

The present invention relates to the preparation of a water-soluble table capable of dissolving without residual particulate matter.

Active ingredients, e.g., pharmacologically active compounds, confectionary products and standards for calibration devices, can be conveniently and economically fabricated into tablets. In order to enable the incorporation of an active ingredient into a tablet, the tablet formulation must have certain characteristics; the ability to flow freely, cohesiveness and lubricity. Because many active compounds do not possess these characteristics, methods of tablet formulation include the incorporation of inert materials known as "additives". These additives include compounds which help to impart satisfactory characteristics to the tablet formulation and include compounds which function as diluents, binders and lubricants.

Diluents include compounds such as dicalcium phosphate, calcium sulfate, lactose, kaolin, mannitol, sodium chloride and powdered sugar. Binders impart cohesiveness to tablet formulations and include compounds such as starch, gelatin, sugars and gums. Other binders include polyethylene glycol, waxes and ethylcellulose.

Lubricants improve the rate of flow, prevent adhesion of the tablet material to the surface of the dies and punches, and reduce "static" and interparticle friction. During mixing or compressing of the formulation, or during ejection of the tablet from the die, an undesirable static charge may occur. Examples of lubricants suggested in the prior art are magnesium stearate, calcium stearate, talc, polyethylene glycol and sodium lauryl sulfate.

Generally two methods are used in table formulation; the wet granulation method and the dry granulation method. The wet granulation method usually involves mixing together the active ingredient, along with a diluent. Solutions of a binding agent are added to form a "wet" mixture. The mixture is then dried, a dry lubricant added, and the mixture compressed into a tablet.

The dry granulation method usually involves mixing together the active ingredient and, if required, a diluent, and part of the lubricant. The mixture is granulated and the remaining lubricant added, blended, and the mixture compressed into tablets.

The simplest tableting machines available are those having the single-punch design. Formation of a tablet on a single-punch tablet press is accomplished as described below. Single punch tablet presses are operated by filling a feed shoe with the tablet composition and emptying the feed shoe into a die cavity. The feed shoe is retracted and scrapes all excess composition away from the die cavity. An upper punch compresses the granulation within the die cavity. After compression, the upper punch retracts and a lower punch rises and ejects the tablet. As the feed show returns to fill the die cavity, it pushes the compressed tablet from the die.

As the name indicates, water-soluble tablets contain various soluble components. It is important for aesthetic reasons that complete dissolution occur, and that no particulate residue or visible foam remain after the tablet is dissolved.

In the process of manufacturing water-soluble tablets, the prior art lubricants such as magnesium and calcium stearate, talc, polyethylene glycol and sodium lauryl sulfate each have disadvantages. The stearates and talc are relatively insoluble and tend to inhibit the rate of dissolution of the water-soluble tablet and cause the resulting solution to appear cloudy because of the presence of undesirable particulate residue. Polyethylene glycol has an undesirably low melting point, while sodium lauryl sulfate can produce excessive foam when the water-soluble tablet is dissolved, which may remain visible on the solution surface.

2. Description of the Prior Art

U.S. Pat. No. 3,692,896 describes the preparation of a water-soluble tablet produced by a process designated as "direct compression" of the active ingredient. Direct compression involves compressing tablets directly from powdered material with the use of only a small amount of additives, e.g., diluents or lubricants. The patent teaches the use of super micro particulate powder of polyethylene glycol having a particle size of less than $50\mu$, preferably $1-10\mu$ and $1-5\mu$.

SUMMARY OF THE INVENTION

The present invention is directed to an improved water-soluble tablet which includes sodium propionate or a combination of sodium propionate and polyethylene glycol.

DETAILED DESCRIPTION OF THE INVENTION

The present invention is directed to the use of sodium propionate, or a combination of sodium propionate and polyethylene glycol in a tablet composition. The sodium propionate used along provides excellent lubricating properties to the composition. Addition of polyethylene glycol to the sodium propionate not only provides additional lubricating properties, but also reduces the "static" which can occur at certain concentrations of lubricants, as is described in greater detail hereinafter.

As indicated earlier, a lubricant is added to a tablet formulation to impart a satisfactory compression characteristic, i.e., lubricity, which is lacking in the active ingredient. The amount required to reduce interparticle friction during compression, and friction between the tablet and die wall during ejection will depend upon the characteristics of the active ingredients. Sodium propionate can be present in a tablet formulation in an amount of from about 3 to 13 percent, weight percent, based on the weight of the tablet. A preferred range is from about 3 to 10 percent by weight.

Addition of from about 0.5 to 5 percent by weight of polyethylene glycol to sodium propionate appears to reduce the formation of a static charge which may occur and to improve the lubricating properties of the total formulation. The presence of polyethylene glycol in a sodium propionate:polyethylene glycol combination in an amount greater than about 5 percent by weight of the total formulation is undesirable in that it may produce sufficient softening of the formulation during compression to cause sticking of the tablet within the die cavity.

It had been determined that the sodium propionate:polyethylene glycol combination functions best when the amount of polyethylene glycol does not exceed the amount of sodium propionate. The sodium propionate:polyethylene glycol can be present in a ratio of from about 1:1 to about 10:1. A preferred ratio is about 5:1 sodium propionate:polyethylene glycol. The desired amount of sodium propionate or sodium propionate:-polyethylene glycol combination to be added can be easily determined by one skilled in the art, by preparing tablet formulations containing sodium propionate, or sodium propionate and polyethylene glycol and determining the level of lubricity required.

The particle size of the sodium propionate and polyethylene glycol is not extremely critical. Sodium propionate is commercially available in various particle sizes. A particle size of about 75μ has been found to be convenient and economical. Polyethylene glycol is commercially available in particle sizes which range from extremely fine, e.g., 1μ, to greater than 250μ. A particle size of about 150μ has been found to be convenient to use in the present invention. Use of sodium propionate or polyethylene glycol smaller than 50μ particle size may introduce fines which can retard the flow. Use of sodium propionate or polyethylene glycol greater than 250μ particle size may cause inadequate dispersion of the lubricant within the tablet formulation.

Tablets are popular because of the simplicity and economy in fabrication, and stability and convenience in dispensing and shipping. The advantages to the consumer include accuracy and compactness and portability. Because of these advantages, tablets are useful in such diverse applications as incorporating pharmaceutical dosages, providing a $CO_2$ atmosphere for cell culture, providing desired pH ranges for calibration of instruments, denture cleansers and many other uses. Water-soluble tablets suitable for pharmaceutical dosages containing sodium propionate or a combination of sodium propionate and polyethylene glycol include: antacids, analgesics, ascorbic acid, acetylsalicyclic acid, steroids, diuretics and hypnotics and sedatives.

Examples I and II illustrate the use of the present invention in a water-insoluble tablet for providing release of $CO_2$.

EXAMPLE 1

Tablets were prepared with two strongly abrasive compounds, sodium bicarbonate and citric acid mixed together with sodium propionate in the proportions indicated below:

|  | milligram (mg)/tablet | Percent |
| --- | --- | --- |
| Sodium bicarbonate | 140 | 70 |
| Citric acid | 40 | 20 |
| Sodium propionate (~75μ) | 20 | 10 |
|  | 200 |  |

The above ingredients were mixed together dry and formed into tablets on a single punch Colton T-2 tablet press with an upper punch pressure of about 1.75 tons. A stainless steel flat bevelled round punch (5/16" diameter) was used. The tablet produced had a diameter of about 3.8 millimeter. Each tablet contained 10 percent by weight of sodium propionate. Approximately 200 tablets were prepared and tested.

Visual inspection of tablets formed was made to determine the degree of lubricant protection, by observing tablet surface quality. The degree of lubricant protection was also determined by observing various tablet press characteristics.

If the lubricant amount was unsatisfactory, scraping and grinding within the punch and die resulted during compression or the composition would stick to the punch surfaces. An insufficient amount of lubricant produces unacceptable furrows or lines on the tablet side ("scoring") or tablet surface pitting.

Observation of the production of tablets produced as described above indicated that ejection of the tablets from the press appeared normal. The tablets formed were glossy and had an elegant smooth surface; no pitting or scoring was detected.

Tablet hardness was determined with a hand model Pfizer hardness measuring device. The instrument operates on the same mechanical principle as ordinary pliers. The force required to break a tablet is recorded on a dial, expressed as either kilograms or pounds of force. A hardness of about 3.5 to 4 kilograms is considered satisfactory.

The tablets produced as described above had a hardness in the range of from 3.5 to slightly less than 4 kilograms.

When the tablets weere placed in water, the tablets dissolved quickly with the evolution of $CO_2$, to form a clear solution after $CO_2$ evolution ceased. No particulate residue remained in the solution.

EXAMPLE II

A $CO_2$-producing tablet was prepared as described in Example 1, except that 3 percent by weight of sodium propionate was present. The composition showed good lubrication and flow properties during tablet production. The tablets were glossy and had a hardness of about 4 kilograms.

When the tablets were placed into water, the tablets dissolved quickly with the evolution of $CO_2$, to form a clear solution after $CO_2$ evolution ceased. No particulate residue remained in the solution.

A formulation similar to the formulation of Example I was used, except that a microcrystalline cellulose powder, which functions to increase tablet hardness, was added.

EXAMPLE III

|  | mg/tablet | Percent |
| --- | --- | --- |
| Sodium bicarbonate | 130 | 65 |
| Citric acid | 40 | 20 |
| Sodium Propionate | 20 | 10 |
| Cellulose powder | 10 | 5 |
|  | 200 |  |

The microcrystalline cellulose, powder, having a particle size of about 90μ, is commercially available from FMC Corporation, New York, New York under the trade designation Avicel H102.

The above ingredients were mixed together dry and formed into tablets as described in Example 1.

As in Example 1, ejection of the tablets appeared normal. The tablets formed were glossy and had an elegant smooth surface. The tablets had a slightly increased hardness of greater than 4 kilograms. The tablets dissolved in water with the evolution of $CO_2$. The cellulose powder imparted a slight cloudiness to the solution.

EXAMPLE IV

|  | mg/tablet | Percent |
| --- | --- | --- |
| Sodium barbital | 65 | 43.3 |
| Lactose | 65 | 43.3 |

-continued

|  | mg/tablet | Percent |
|---|---|---|
| Sodium propionate | 20 | 13.3 |
|  | 150 |  |

The abovee ingredients were mixed together dry and formed into a number of tablets. Each tablet contained approximately 13 percent by weight sodium propionate. The lactosee was present as a diluent and also functioned as a binder to impart a cohesive quality to the powdered material.

The tablets produced were glossy and had a hardness of about 4 kilograms. When the tablets were placed into water they dissolved with shaking, leaving a clear solution.

EXAMPLE V

A number of $CO_2$-producing tablets, having the following composition, were prepared as described in Example I.

|  | Tablet Formulation #1 | |
|---|---|---|
|  | mg | % |
| Sodium bicarbonate | 92.50 | 61.7 |
| Citric acid | 50.75 | 33.8 |
| Sodium propionate | 4.50 | 3.0 |
| Polyethylene glycol | 2.25 | 1.5 |
|  | 150.00 |  |
| Sodium propionate:polyethylene glycol ratio | 2:1 | |

The composition of Formulation #1 had excellent lubricating properties; little or no static charge was present. The tablets were smooth and glossy, with no scoring marks present. The tablets had a hardness of about 4 kilograms and dissolved in water leaving a clear solution.

For comparative purposes, tablets were prepared having the compositions described below, to investigate the effect of decreasing the sodium propionate below 3 percent while increasing the sodium propionate: polyethylene glycol ratio above 1:1.

| Comparative Procedure A | | | | |
|---|---|---|---|---|
|  | Tablet Formulation #2 | | Tablet Formulation #3 | |
|  | mg | % | mg | % |
| Sodium bicarbonate | 92.50 | 61.7 | 90.25 | 60.2 |
| Citric Acid | 50.75 | 33.8 | 50.75 | 33.8 |
| Sodium propionate | 2.25 | 1.5 | 2.25 | 1.5 |
| Polyethylene glycol | 4.50 | 3.0 | 6.75 | 4.5 |
|  | 150.00 | | 150.00 | |
| Sodium propionate: polyethylene glycol ratio | 1:2 | | 1:3 | |

The comparative tablet compositions of Formulations #2 and #3 had inferior lubricating properties, as evidenced by scoring on the side of the tablets.

These results indicate that if sodium propionate is decreased below 3 percent, even though the sodium propionate:polyethylene glycol ratio is greater than 1:1, the lubricating properties become unsatisfactory.

As described below, a further series of tablets was prepared containing varying amounts of sodium propionatee and polyethylene glycol, along with lactose, to simulate an active ingredient.

EXAMPLE VI

Tablets having the following compositions were prepared as described in Example I.

|  | Tablet Formulation #4 | | Tablet Formulation #5 | | Tablet Formulation #6 | | Tablet Formulation #7 | | Tablet Formulation #8 | |
|---|---|---|---|---|---|---|---|---|---|---|
|  | mg | % | mg | % | mg | % | mg | % | mg | % |
| Lactose | 136.4 | 90.9 | 136.4 | 90.9 | 136.4 | 90.9 | 136.36 | 90.9 | 136.36 | 90.0 |
| Sodium propionate | 6.8 | 4.5 | 9.09 | 6.0 | 11.36 | 7.5 | 12.4 | 8.2 | 13.63 | 10.0 |
| Polyethylene glycol | 6.8 | 4.5 | 4.50 | 3.0 | 2.27 | 1.5 | 1.24 | 0.82 | — | — |
|  | 150.0 | | 149.99 | | 150.03 | | 150.00 | | 149.99 | |
| Sodium propionate:polyethylene glycol ratio | 1:1 | | 2:1 | | 5:1 | | 10:1 | | — | |

The above tablet formulations #4 through #7, having from about 4 to 8 percent sodium propionate and from 0.8 to 4.5 percent polyethylene glycol and having a sodium propionate:polyethylene glycol ratio of from 1:1 to 10:1, possessed satisfactory lubricating characteristics. The tablets produced had a satisfactory hardness and were glossy in appearance. Sample #8 having 10 percent sodium propionate possessed satisfactory lubrication characteristics and was similar to tablets of Example III and IV.

For comparative purposes, tablets were prepared having the compositions described below to investigate the effect of decreasing the amount of sodium propionate below 3 percent, similar to the procedure of Example V.

| Comparative Procedure B | | | | | | |
|---|---|---|---|---|---|---|
|  | Tablet Formulation #9 | | Tablet Formulation #10 | | Tablet Formulation #11 | |
|  | mg | % | mg | % | mg | % |
| Lactose | 143.19 | 95.4 | 143.19 | 95.4 | 143.19 | 95.4 |
| Sodium propionate | 2.27 | 1.5 | 1.14 | 0.75 | .64 | 0.4 |
| Polyethylene glycol | 4.54 | 3.0 | 5.68 | 3.8 | 6.18 | 4.1 |
|  | 150.00 | | 150.01 | | 150.01 | |
| Sodium propionate: polyethylene glycol ratio | 1:2 | | 1:5 | | 1:10 | |

The comparative compositions of formulations #9 through #11 had inferior lubricating properties, as evidenced by sticking of the lower punch to the die cavity wall. Severe scoring on the side of the tablets occurred.

These results indicate that if the amount of polyethylene glycol exceeds the amount of sodium propionate present, the lubricating properties become unsatisfactory.

What is claimed is:

1. In a water-soluble tablet comprising one or more active ingredients, additives and one or more lubricants, the improvement wherein sodium propionate is present.

2. A tablet as claimed in claim 1 wherein the sodium propionate is present in an amount of from about 3 percent to 13 percent by weight, based upon the weight of the tablet.

3. A tablet as claimed in claim 1 wherein the sodium propionate is present in an amount of from about 3 to 10 percent by weight, based upon the weight of the tablet.

4. A tablet as claimed in claim 1 wherein the sodium propionate has a particle size of from about 50 to 250 microns.

5. In a water-soluble tablet comprising one or more active ingredients, additivees and one or more lubricants, the improvement wherein sodium propionate and polyethylene glycol are present, with the proviso that the amount of sodium propionate is at least as great as the amount of polyethylene glycol.

6. A tablet as claimed in claim 5 wherein the sodium propionate and polyethylene glycol are present in a range of from 1:1 to 10:1, sodium propionate:polyethylene glycol based on the weight of the tablet.

7. A tablet as claimed in claim 5 wherein the sodium propionate is present in an amount of from about 3 percent to 8 percent by weight and the amount of polyethylene glycol is present in an amount of from about 0.5 percent to 5 percent by weight, in a range of from about 1:1 to 10:1 sodium propionate:polyethylene glycol, based on the weight of the tablet.

8. A tablet as claimed in claim 5 wherein the sodium propionate and polyethylene glycol have a particle size of from about 50 to 250 microns.

* * * * *

UNITED STATES PATENT AND TRADEMARK OFFICE
CERTIFICATE OF CORRECTION

PATENT NO. : 4,347,235
DATED : August 31, 1982
INVENTOR(S) : Louis G. Daunora

It is certified that error appears in the above-identified patent and that said Letters Patent are hereby corrected as shown below:

Column 3, line 36, "water-insoluble" should read --water-soluble--.

Signed and Sealed this

Eleventh Day of October 1983

[SEAL]

Attest:

GERALD J. MOSSINGHOFF

Attesting Officer    Commissioner of Patents and Trademarks